United States Patent
Ina et al.

(10) Patent No.: US 7,916,271 B2
(45) Date of Patent: Mar. 29, 2011

(54) APPARATUS AND METHOD FOR SPECIFYING CORRELATION, EXPOSURE APPARATUS, AND DEVICE MANUFACTURING METHOD

(75) Inventors: Hideki Ina, Utsunomiya (JP); Satoru Oishi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 276 days.

(21) Appl. No.: 11/489,360

(22) Filed: Jul. 19, 2006

(65) Prior Publication Data

US 2007/0019857 A1 Jan. 25, 2007

(30) Foreign Application Priority Data

Jul. 20, 2005 (JP) ................. 2005-210320

(51) Int. Cl.
*G03B 27/42* (2006.01)
(52) U.S. Cl. .......................... 355/53; 356/400
(58) Field of Classification Search .................. 356/401; 700/108, 109; 355/30, 53
See application file for complete search history.

(56) References Cited

U.S. PATENT DOCUMENTS

| | | | | |
|---|---|---|---|---|
| 2003/0204348 A1* | 10/2003 | Suzuki et al. | ................... | 702/83 |
| 2006/0047454 A1* | 3/2006 | Tamaki et al. | ................... | 702/84 |

FOREIGN PATENT DOCUMENTS

| | | | |
|---|---|---|---|
| JP | 2001167996 A | * | 6/2001 |
| JP | 2004-031929 | | 1/2004 |

OTHER PUBLICATIONS

Translation of JP 2001-167996 is attached (or submitted with this office action).*

* cited by examiner

*Primary Examiner* — Edward J Glick
*Assistant Examiner* — Mesfin T Asfaw
(74) *Attorney, Agent, or Firm* — Cowan, Liebowitz & Latman, P.C.

(57) ABSTRACT

Disclosed is a method and apparatus which are arranged to detect magnitude of correlation between (i) an explanatory variable corresponding to operation data related to an operation made by an exposure apparatus for exposing a substrate, and (ii) a response variable corresponding to inspection data related to a result of inspection made to the substrate after the same is exposed, the magnitude of correlation between the explanatory variable and the response variable being detected with respect to each of different combinations of operation data pieces, and also arranged to specify, on the basis of detected correlation magnitudes and with respect to one of the different combinations of operation data pieces, a category of the operation data and the correlation between the explanatory variable and the response variable.

11 Claims, 6 Drawing Sheets

(a)

```
      P1        P2        P3
 1    0.6036   1.289524  0.150079
 2  0.818227  8.392137  0.744941
 3  0.817011  3.449372  3.259959
 4  0.039417  6.327394  8.907268
 5  0.176324  9.956645  3.919117
 6  0.083309  4.701949  1.132137
 7  0.124723  3.137419  8.306602
 8  0.788679  0.446087  6.441887
 9  0.924899  7.302549  9.926396
10    0.52579  7.967131  5.672859
11  0.000903  2.304842  0.173243
12  0.147996   3.62796  2.835581
13  0.513129  1.675136  6.436441
14  0.460399   9.70467  6.179041
15  0.703691  6.226208  7.348533
16  0.279308   4.12729  3.384363
17  0.503031  7.095206  5.983381
18   0.19938  3.451276  2.640842
19  0.438094  1.655772  5.841072
20  0.286674  4.033148  4.148126
21  0.595671  3.575188  6.551574
22  0.625239  4.053708  7.612408
23  0.180203  4.625999  3.780125
24  0.246895  1.592762  4.396239
25  0.094709   2.23699  1.650695
26  0.562365  4.109574  6.023588
27  0.641416  4.263517  7.832634
28  0.930615   8.70809   8.51206
29  0.855577  9.988453  1.480139
30  0.457584   0.92026  9.453463
31  0.098639  9.552877  2.822408
32  0.853484  0.655477   5.36467
33  0.783762   6.84946  9.834612
34  0.424068  6.761505   0.17026
35  0.624662  3.607031  7.341832
36  0.642554  2.410294  1.233511
37  0.639743  6.496314  4.577363
38  0.225766  0.641929  2.111816
39  0.137664  5.290554  1.427478
40  0.048257  6.549555  4.245837
41  0.483985  9.994342  6.527108
42  0.679135   5.92248  3.765789
43  0.342344  4.588261  2.633385
44  0.423893  4.745151  8.924003
45  0.845095  5.265893  0.318008
46  0.164527  7.289434  9.344789
47  0.514685  0.494149  4.491231
48  0.173734   6.87808  8.105566
```

(b) CORRELATION BY ALL DATA (c) CORRELATION BY HALF DATA (d) CORRELATION BY QUARTER DATA (a)

| | P1 | P2 | P3 | P4 |
|---|---|---|---|---|
| 1 | 0.6036 | 1.289524 | 0.150079 | STI |
| 2 | 0.818227 | 8.392137 | 0.744941 | STI |
| 3 | 0.817011 | 3.449372 | 3.259959 | STI |
| 4 | 0.039417 | 6.327394 | 8.907268 | STI |
| 5 | 0.176324 | 9.956645 | 3.919117 | STI |
| 6 | 0.083309 | 4.701949 | 1.132137 | STI |
| 7 | 0.124723 | 3.137419 | 8.306602 | STI |
| 8 | 0.788679 | 0.446087 | 6.441887 | STI |
| 9 | 0.924899 | 7.302549 | 9.926396 | STI |
| 10 | 0.52579 | 7.967131 | 5.672859 | STI |
| 11 | 0.000903 | 2.304842 | 0.173243 | STI |
| 12 | 0.147996 | 3.62796 | 2.835581 | STI |
| 13 | 0.513129 | 1.675136 | 6.436441 | M1 |
| 14 | 0.460399 | 9.70467 | 6.179041 | M1 |
| 15 | 0.703691 | 6.226208 | 7.348533 | M1 |
| 16 | 0.279308 | 4.12729 | 3.384363 | M1 |
| 17 | 0.503031 | 7.095206 | 5.983381 | M1 |
| 18 | 0.19938 | 3.451276 | 2.640842 | M1 |
| 19 | 0.438094 | 1.655772 | 5.841072 | M1 |
| 20 | 0.286674 | 4.033148 | 4.148126 | M1 |
| 21 | 0.595671 | 3.575188 | 6.551574 | M1 |
| 22 | 0.625239 | 4.053708 | 7.612408 | M1 |
| 23 | 0.180203 | 4.625999 | 3.780125 | M1 |
| 24 | 0.246895 | 1.592762 | 4.396239 | M1 |
| 25 | 0.094709 | 2.23699 | 1.650695 | Via |
| 26 | 0.562365 | 4.109574 | 6.023588 | Via |
| 27 | 0.641416 | 4.263517 | 7.832634 | Via |
| 28 | 0.930615 | 8.70809 | 8.51206 | Via |
| 29 | 0.855577 | 9.988453 | 1.480139 | Via |
| 30 | 0.457584 | 0.92026 | 9.453463 | Via |
| 31 | 0.098639 | 9.552877 | 2.822408 | Via |
| 32 | 0.853484 | 0.655477 | 5.36467 | Via |
| 33 | 0.783762 | 6.84946 | 9.834612 | Via |
| 34 | 0.424068 | 6.761505 | 0.17026 | Via |
| 35 | 0.624662 | 3.607031 | 7.341832 | Via |
| 36 | 0.642554 | 2.410294 | 1.233511 | Via |
| 37 | 0.639743 | 6.496314 | 4.577363 | M2 |
| 38 | 0.225766 | 0.641929 | 2.111816 | M2 |
| 39 | 0.137664 | 5.290554 | 1.427478 | M2 |
| 40 | 0.048257 | 6.549555 | 4.245837 | M2 |
| 41 | 0.483985 | 9.994342 | 6.527108 | M2 |
| 42 | 0.679135 | 5.92248 | 3.765789 | M2 |
| 43 | 0.342344 | 4.588261 | 2.633385 | M2 |
| 44 | 0.423893 | 4.745151 | 8.924003 | M2 |
| 45 | 0.845095 | 5.265893 | 0.318008 | M2 |
| 46 | 0.164527 | 7.289434 | 9.344789 | M2 |
| 47 | 0.514685 | 0.494149 | 4.491231 | M2 |
| 48 | 0.173734 | 6.87808 | 8.105566 | M2 |

(b) OFFSET VS SIGNAL SYMMETRY@M1
$y = 8.7457x + 1.6913$
$R^2 = 0.9064$

APPARATUS AND METHOD FOR SPECIFYING CORRELATION, EXPOSURE APPARATUS, AND DEVICE MANUFACTURING METHOD

FIELD OF THE INVENTION AND RELATED ART

This invention relates to an exposure apparatus and an exposure method which are usable to produce, through a lithographic process, devices with a fine pattern such as semiconductor chips (ICs or LSIs), liquid crystal display devices, thin-film magnetic heads, or micromachines, for example. More particularly, the invention is directed to an exposure apparatus and an exposure method by which the productivity of devices can be improved significantly.

The manufacture of semiconductor devices, liquid crystal display devices or thin-film magnetic heads, for example, which is based on a lithographic process uses a projection exposure apparatus having a structure for projecting and imaging, through a projection optical system, a pattern image of a mask or a reticle (hereinafter, simply "reticle") onto a photosensitive substrate.

In recent years, the resolved linewidth is becoming smaller and smaller to meet higher integration density of a semiconductor device, and this has developed enlargement of the numerical aperture (NA) of projection exposure lenses, shortening of the wavelength of used light sources and enlargement in size of the picture plane. In order to achieve these, at first, exposure apparatuses called a "stepper" having a structure for simultaneously projecting an exposure region of approximately square shape onto a wafer in a reduced scale have been used. Nowadays, however, exposure apparatuses called a "scanner" are being mainly used, in which apparatuses an exposure region of oblong slit-like shape is used and a reticle and a wafer are relatively scanned at a high speed whereby a large-size picture plane can be exposed with good precision.

In the scanner type exposure apparatuses, the surface shape of the wafer can be brought into registration with the best exposure image plane position in the unit (precision) of the scan exposure slit. Therefore, this method has an advantage of reduced influence of wafer flatness.

In the scanner type exposure apparatuses, exposure is carried out in the unit of the scan exposure slit. To this end, the height (level) of the wafer surface portion to which the exposure slit is going to be projected, which portion may include tilt, is measured just before the exposure, and then the exposure is carried out on the basis of the information obtained by the measurement. Hence, in scanner type exposure apparatuses as compared with stepper type exposure apparatuses, a great number of height (level) measurement operations are carried out. Here, this height measurement will hereinafter be referred to as "focus measurement".

Even in cases where such a scanner is used, the depth of focus is very small because the NA has been enlarged to meet the trend of miniaturization of the exposure patterns. Also, the precision for registration of the wafer surface, to be exposed, with the best imaging plane, that is, focus precision, is very severe. Furthermore, accurate alignment precision is required as well. In addition to these precisions, high throughput should be satisfied at the same time.

In order to meet these requirements of higher precision and higher throughput, in some systems called "APC" or "AEC", for error analysis in the exposure apparatus, exposure hysteresis data and inspection data are stored in a database, and error analysis which may include taking correlation between these data is carried out. The exposure hysteresis data can be classified into control variables and measurement data.

The control variables are variables that can be changed in relation to control of the exposure apparatus. Examples of them are the type of alignment marks, illumination wavelength (center and width thereof), and sampling points for focus measurement. Examples of the measurement data are alignment measured value and focus measured value which are measured by the apparatus in the exposure operation.

The inspection data may include an alignment (overlay) measurement result and a CD (linewidth) measurement result as measured by using inspection tools.

In these days, in some applications, the exposure hysteresis data and the inspection data are stored into a database and, when a problem occurs, the data is statistically analyzed to solve the problem. Particularly, software programs have been developed to extract an unknown phenomenon (the process being called "data mining"), and actually this plays a role in analyzing deterioration factors in semiconductor exposure apparatuses.

As described above, correlation between the exposure hysteresis data and the inspection data may be sought and analyzed for the error analysis in exposure apparatuses. However, the number of pieces of data included there is extraordinarily large. The inventors of the subject application have introduced commercially available latest version of data-mining software programs to find out correlations among quite massive data, and it has been found that there are cases in which any phenomenon that is very important from the standpoint of higher precision and higher throughput cannot be identified only by use of these programs.

SUMMARY OF THE INVENTION

It is accordingly an object of the present invention to provide a unique technique for identifying a correlation between data related to the operation or operations having already been carried out by an exposure apparatus and inspection data concerning each substrate having been exposed thereby.

In accordance with an aspect of the present invention, there is provided an apparatus comprising: detecting means configured to detect magnitude of correlation between (i) an explanatory variable corresponding to operation data related to an operation made by an exposure apparatus for exposing a substrate, and (ii) a response variable corresponding to inspection data related to a result of inspection made to the substrate after the same is exposed, the magnitude of correlation between the explanatory variable and the response variable being detected with respect to each of different combinations of operation data pieces; and specifying means configured to specify, on the basis of detected correlation magnitudes and with respect to one of the different combinations of operation data pieces, a category of the operation data and the correlation between the explanatory variable and the response variable.

In the apparatus according to this form of the present invention, the apparatus may be one of an exposure apparatus for performing an exposure of a substrate to a pattern, an inspection apparatus for inspecting a substrate to which the exposure has been performed, and a host computer for controlling an operation of the exposure apparatus.

In accordance with another aspect of the present invention, there is provided an exposure apparatus for performing an exposure of a substrate to a pattern, said apparatus comprising: a controller configured to control an operation of said exposure apparatus on the basis of information related to a correlation between (i) an explanatory variable corresponding to data related to an operation made by said exposure apparatus and (ii) a response variable corresponding to inspection data related to inspection made to the substrate after the same is exposed; and an apparatus as recited above for specifying the correlation.

In accordance with a further aspect of the present invention, there is provided a method of manufacturing a device, said method comprising steps of: exposing a substrate to a pattern using an exposure apparatus as recited above; developing the exposed substrate; and processing the developed substrate to manufacture the device.

In accordance with a yet further aspect of the present invention, there is provided a method comprising steps of: detecting magnitude of correlation between (i) an explanatory variable corresponding to operation data related to an operation made by an exposure apparatus for exposing a substrate, and (ii) a response variable corresponding to inspection data related to a result of inspection made to the substrate after the same is exposed, the magnitude of correlation between the explanatory variable and the response variable being detected with respect to each of different combinations of operation data pieces; and specifying, on the basis of detected correlation magnitudes and with respect to one of the different combinations of operation data pieces, a category of the operation data and the correlation between the explanatory variable and the response variable.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Preferred embodiments of the present invention will now be described with reference to the attached drawings.

First Embodiment

Figure 1:
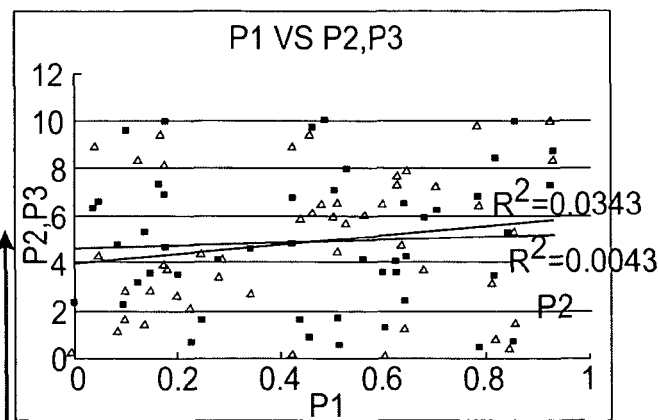
FIG. 1 is a schematic illustration for explaining a first embodiment of the present invention wherein correlation between exposure hysteresis data and inspection data is sought.
Figure 1:
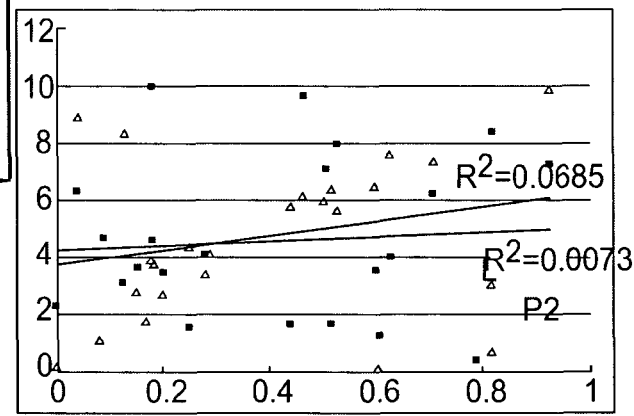
Figure 1:
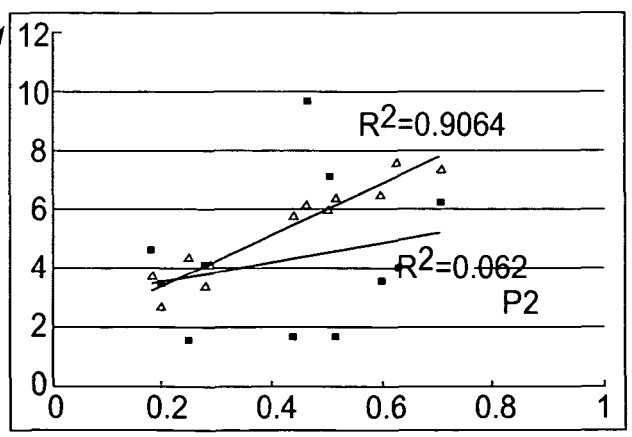

FIG. 1 illustrates exposure hysteresis data, at left-hand portion (a), and correlations at right-hand portions (b), (c) and (d), sought with respect to data pieces of different numbers, respectively.

In FIG. 1, at (a), denoted at P1, P2 and P3 are variables which have been stored in a database in corresponding data piece sets of a number 48.

Here, variable P1 is an alignment offset amount that corresponds to the result of alignment inspection (namely, inspection data for the subject after being exposed by the exposure apparatus). This variable is taken as a response variable. On the other hand, variables P2 and P3 correspond to exposure hysteresis data (that is, data concerning the operation or operations having been carried out by the exposure apparatus). As an example, variable P2 may be a characteristic value (to be described later) based on an alignment measurement signal, and variable P3 may be a value that represents asymmetry of the alignment measurement signal. These variables are taken as explanatory variables. Namely, what is shown at (a) in FIG. 1 is that: the alignment result takes a value at P1 when variables P2 and P3 take the values shown there, and such relationship has already been identified with respect to each of the 48 data pieces.

The graph at (b) in FIG. 1 shows correlations, sought for all the 48 pieces of data, between variable P1 and variables P2 and P3. Solid squares depict the relation between variable P1 and variable P2, and blank triangles depict the relation between variable P1 and variable P3. The R-square ($R^2$) value that represents the magnitude of correlation is 0.004 between P1 and P2, and it is 0.034 between P1 and P3. Although the value for P1 and P3 is larger a little bit, anyway these values are not greater than 0.1 and they cannot be concluded as an evidence of correlation.

The graph at (c) in FIG. 1 shows the results wherein correlations between variable P1 and variables P2 and P3 are sought with respect to 24 pieces of data (a half of all the data pieces). The R-square value is 0.007 with regard to P2, and it is 0.069 with regard to P3. Similarly to the case of all the data, the value for P3 is larger a little bit, but anyway these are not greater than 0.1 and they cannot be concluded as an evidence of correlation.

The graph at (d) in FIG. 1 shows the results wherein correlations between variable P1 and variables P2 and P3 are sought with respect to 12 pieces of data (a quarter of all the data pieces). The R-square value is 0.062 for P2, and it is 0.906 for P3. In this example, the R-square value that represents the correlation of P3 is quite close to 1. Hence, it is seen that definite correlation is present between variable P1 and variable P2.

In this manner, even if all the data pieces are analyzed and the R-square takes a small value, not less than 0.1, such that no correlation can be found there, with the procedure described above the presence of strong correlation can be revealed in respect to a certain portion of all the data, that is, the last one (quarter data) in the example of FIG. 1.

Figure 2:
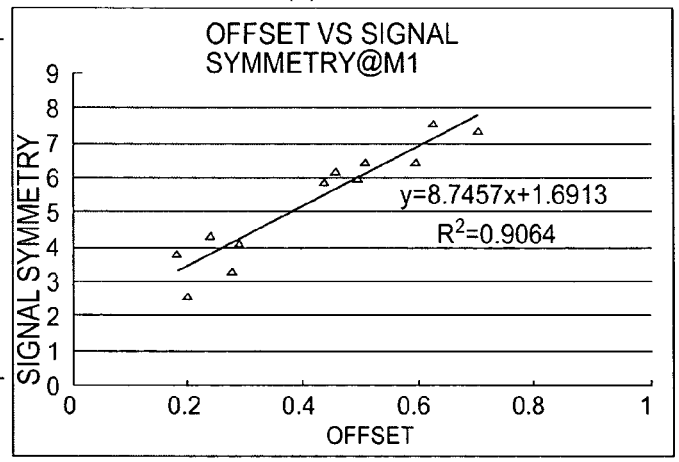
FIG. 2 is a schematic illustration for explaining an array of data pieces obtained as a result of data mining.

Next, what has brought a strong correlation in the quarter data described above is investigated on the basis of data mining with regard to the exposure hysteresis data and the inspection data. As an example, as shown in FIG. 2, the process information that represents the category of exposure operation (e.g., information for categorizing the processes in the device manufacture) is now considered as a variable P4. It is now assumed that, as shown, all the data pieces are classified into four groups (each having 12 data pieces) which correspond to four steps (processes) STI, M1, Vial and M2, respectively. It is seen that, with regard to step M1 in FIG. 2, strong correlation is present between variable P1 and variable P3. Here, as regards the correlation, it is shown that, as long as only step M1 concerns, the alignment offset value (=P1) is being correlated with the value (=P3) representing signal asymmetry, at approx. 8.7 times higher susceptibility. Hence, after alignment measurement is carried out in the exposure apparatus, correction may be made to the thus obtained alignment measured value by using a reciprocal number (=−1/8.7458) to the value representing the asymmetry. With this procedure, high precision alignment of the wafer in step M1 is assured.

In accordance with this embodiment, since the alignment precision can be made higher, the need of any reworks such as applying a resist again to the wafer or of repeated offset inspection can be removed. Therefore, the device yield as well as the apparatus throughput can be improved significantly.

In FIGS. 1 and 2, the number of data piece is 48. However, the present invention is not limited to it. Rather, in relation to data pieces of a further greater number, revealing a particular data group having high correlation would be effective to assure good precision after the correction.

Furthermore, although in FIGS. 1 and 2 all the data is divided up to ¼, the present invention is not limited to this. Dividing data into ⅛ or 1/16 may be similarly effective to accomplish the object of the present invention.

This embodiment has a feature that a hidden one having correlation is revealed by dividing the data. Then, on the basis of the magnitude of that correlation, a control variable or variables (control target data) or measurement data is corrected or, alternatively, the tolerable range for the control variable (control target data) or measurement data is determined. With this procedure, the performance of semiconductor exposure can be improved significantly.

Here, the problem may possibly be solved if the process or the apparatus can be changed on the basis of the correlation so that such correlation is avoided. Practically, however, it is quite difficult to accomplish. Thus, the usefulness of the present invention does reside in that the difficulty is removed simply.

Figure 3:
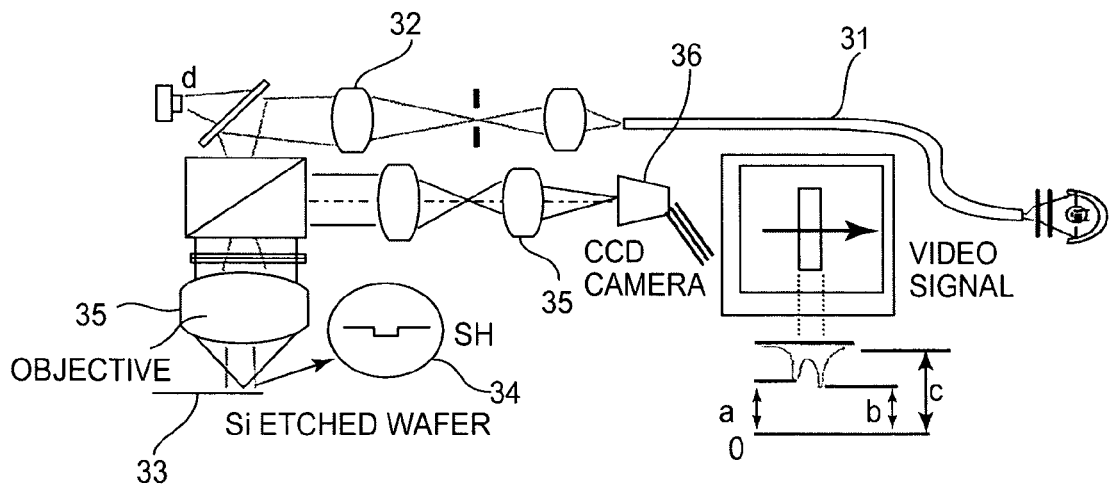
FIG. 3 is a schematic illustration showing an example of alignment detection system of a semiconductor exposure apparatus and a signal obtained thereby.

FIG. 3 shows an example of apparatus which provides variables P2 and P3.

The apparatus shown in FIG. 3 is called "off-axis alignment scope" which is being prevalently used as an alignment detection system in exposure apparatuses after those having a KrF laser as a light source. This alignment scope uses image processing as the detection principle thereof.

More specifically, an alignment mark 34 formed on a wafer 33 is illuminated by an illumination optical system 32, etc. with the light introduced through a fiber 31. An imaging optical system, having an objective lens 35, for example, functions to form an image of the alignment mark upon an image pickup device 36 such as CCD, for example. This image is then photoelectrically converted by the image pickup device 36 into a video signal which is subsequently processed in various ways, whereby the position of the alignment mark is detected.

This video signal is shown in FIG. 3. Now, an example of how variable P2 and P3 can be defined will be explained. In FIG. 3, if the output of the video signal is denoted by c, the bottom output levels are denoted by a and b, and the illumination light quantity (the value as can be measured by a photoelectric converting sensor or the like) is denoted by d, the variables can be expressed as follows:

$P2=c/d$ $P3=a-b$

Since the quantities of variable P3 shown in FIG. 1 are all positive, in the case of this example the output level a of the first bottom (trough) of the W-shaped signal is always larger than the output level b of the second bottom (trough).

Figure 4:
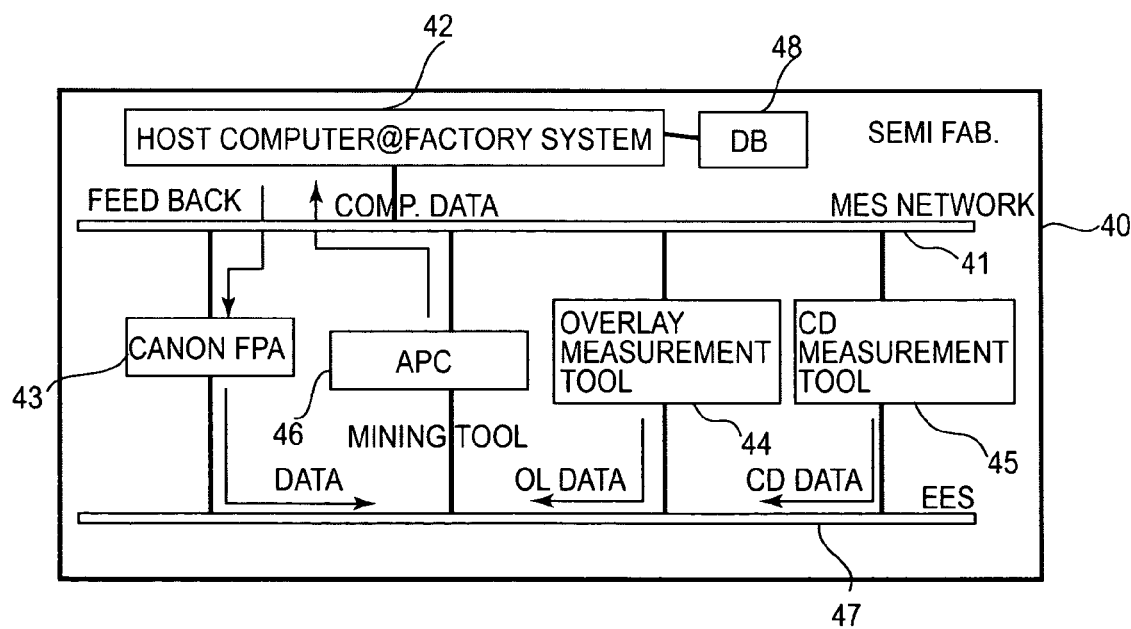
FIG. 4 is a block diagram showing an example of network environment of a semiconductor manufacturing factory.

FIG. 4 shows a network environment of a semiconductor device production site, including a semiconductor exposure apparatus and inspection machines.

There is a network 41 called "MES" (Manufacturing Execution System) and, by using this, a host computer 42 controls all the machines inside the semiconductor manufacturing factory 40. In FIG. 4, denoted by "FPA" is a semiconductor exposure apparatus 43 which is arranged to perform exposure in accordance with instructions supplied from the host computer 42. There is an overlay measurement tool 44 for inspecting the result of alignment as well as a CD overlay measurement tool 45 for inspecting the linewidth, and these are connected to the host computer 42. Inspection data obtained by these tools is stored into a database (DB) 48 inside the host computer, through a software 46 called "APC" (Advanced Process Control).

In the present invention, the data mining may be carried out in this APC or it may be done by the host computer. In the structure shown in FIG. 4, it is carried out by the APC, and the exposure hysteresis data of the exposure apparatus as well as the inspection data from the overlay measurement tool 44 and the CD overlay measurement tool 45 are supplied into the APC through a network 46 called "EES" (Engineering Equipment System).

When the procedure according to the present invention is carried out inside the APC and if a significant correlation is revealed under a certain condition, on the basis of judgment made by the host computer an appropriate procedure is carried out to the semiconductor exposure apparatus FPA in accordance with the detected correlation. If there is an explanatory variable or variables found in relation to the strong correlation, such explanatory variable or variables may be configured inside the semiconductor exposure apparatus FPA as a variable for setting the control variable of the semiconductor exposure apparatus.

Other Embodiments

Figure 5:
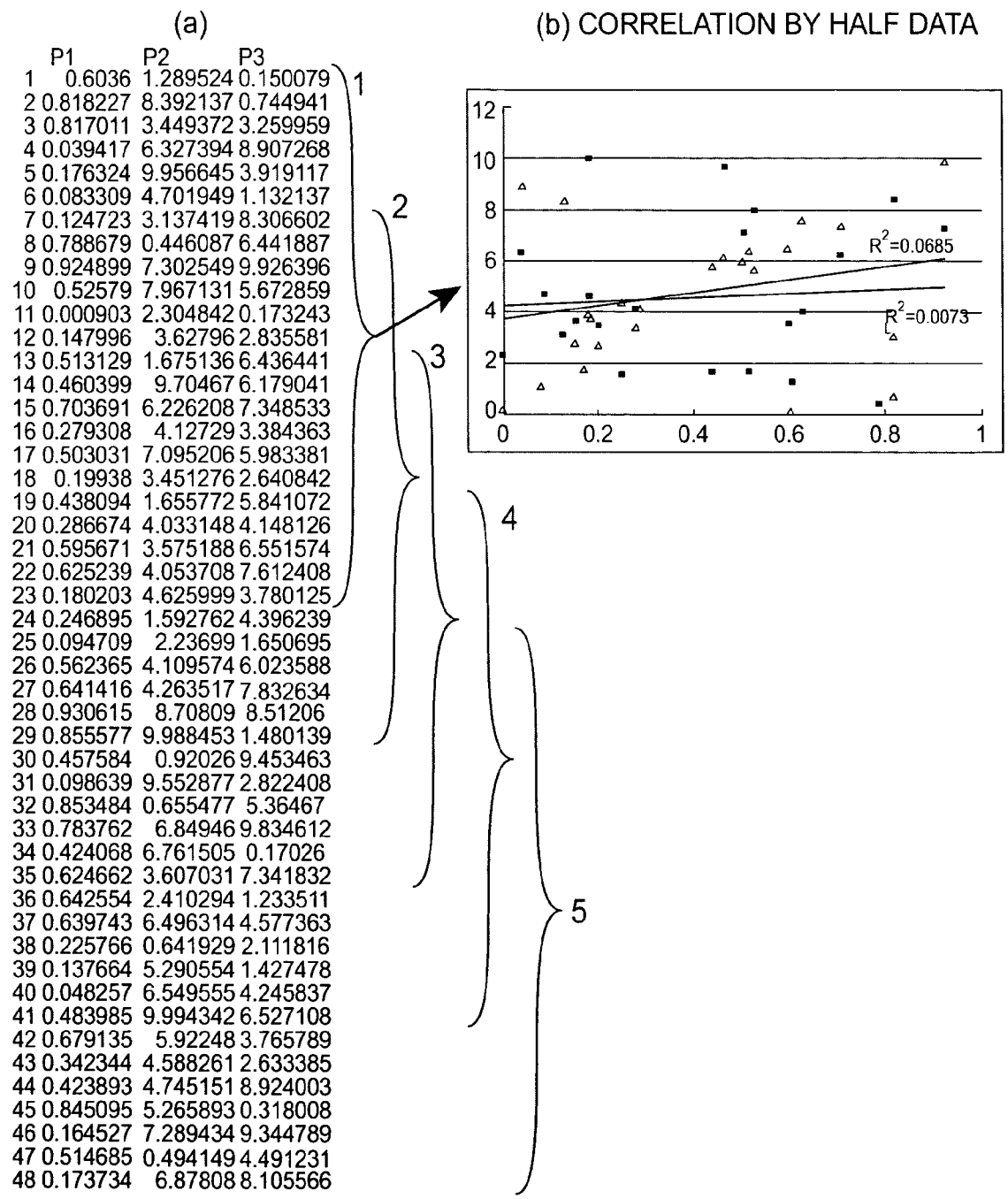
FIG. 5 is a schematic illustration for explaining a second embodiment of the present invention wherein correlation between exposure hysteresis data and inspection data is sought.
Figure 6:
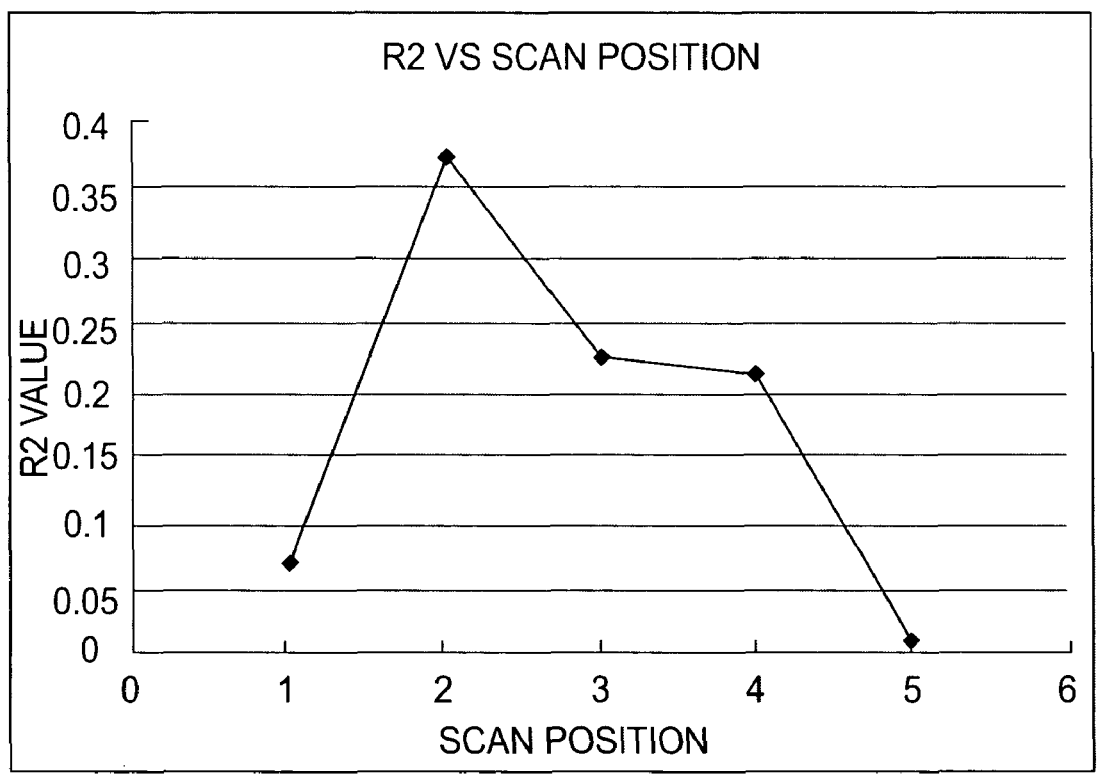
FIG. 6 is a graph for explaining the magnitude of correlation and a correlation function.

Referring now to FIGS. 5 and 6, other embodiments of the present invention will be explained.

The measurement data may include measured values related to alignment or focus, X, Y and Z driving amounts of the wafer stage, and exposure amount. Furthermore, year, month, date, day of the week, time, temperature, pressure, humidity, machine ID, operators and so on may be included there. Yet further, the timing of resetting the exposure machine or process machine as well as timing of maintenance for them may be included there.

The inspection data may include alignment (overlay) measurement result or CD measurement result having been measured by inspection tools. Furthermore, wafer magnification, rotational error, image plane tilt and so on, which are obtainable from calculations made to the overlay measurement result while taking into account the control variables or inspection conditions, may be included there. In this embodiment, while all of these are taken as response variables, the object can be accomplished in accordance with data mining.

In the example described above, the data mining is carried out inside the APC shown in FIG. 4. However, the present invention is not limited to this. For example, it may be carried out inside the overlay measurement tool 44, or alternatively, it may be performed inside the semiconductor exposure apparatus (FPA) 43. The object of the present invention can be accomplished also in theses cases. As a further alternative, the procedure related to the alignment may be carried out inside the overlay measurement tool 44 while the procedure related to the focus may be carried out inside the CD overlay measurement tool 45, independently of each other. In that occasion, exposure hysteresis data or the like necessary for these procedures, respectively, may preferably be introduced through the EES 47 or MES 41, into a unit where the data mining is going to be done.

The database (DB) may be single and prepared in the host computer 42. Alternatively, a plurality of databases may be prepared in the FPA 43, APC 46, overlay measurement tool 44, CD overlay measurement tool 45, for example, respectively. Anyway, the object of the present invention can be accomplished by that.

When all the data is sequentially halved to fine out a correlation therein as shown in FIG. 2, it is not always possible that significant correlation is revealed by the number of data pieces just divided, as in the case of M1. What is important there is that, during successive divisions, the moment at which the magnitude of correlation changes should be detected. When the magnitude of correlation has just changed, the number of data pieces to be processed may be increased or decreased, and data mining may be done to identify whether there is some corresponding information in other data such as exposure hysteresis data, for example. The object of the present invention can be accomplished with this procedure as well.

The object of the present invention can be achieved not only by sequentially halving all the data but also by sequentially changing the data combination for seeking correlation, as shown in FIG. 5, while keeping the number of data pieces unchanged. In FIG. 1, the correlation is sought while sequentially halving the data number. In FIG. 5, on the other hand, the correlation is sought five times while shifting the data processing range, covering a half of all the data, step-by-step by ⅛ of all the data number.

The graph of FIG. 6 shows the results of changes of the R-square correlation magnitude between variable P1 and variable P3, in this example. In data region 2, the R-square correlation magnitude is approx. 0.37 and it takes a peak value. Here, in the vicinity of this data region 2, correlation may be sought again while changing the number of used data pieces. With this procedure, a data region having strong correlation could be found as in the case of FIG. 2.

In accordance with the embodiments of the present invention as described hereinbefore, in the semiconductor manufacture using an exposure apparatus, very useful data which is hidden in massive exposure hysteresis data or inspection data and which cannot be revealed by conventional data mining can be found out quite efficiently. As a result of this, the alignment (overlay) precision or CD precision in semiconductor manufacture can be improved remarkably, such that the yield can be increased without degrading the throughput.

Embodiment of Device Manufacture

Next, an embodiment of a device manufacturing method for producing microdevices such as semiconductor chips (ICs or LSIs), liquid crystal panels, CCDs, thin-film magnetic heads or micromachines, for example, by using an exposure apparatus described above, will be explained.

Figure 7:
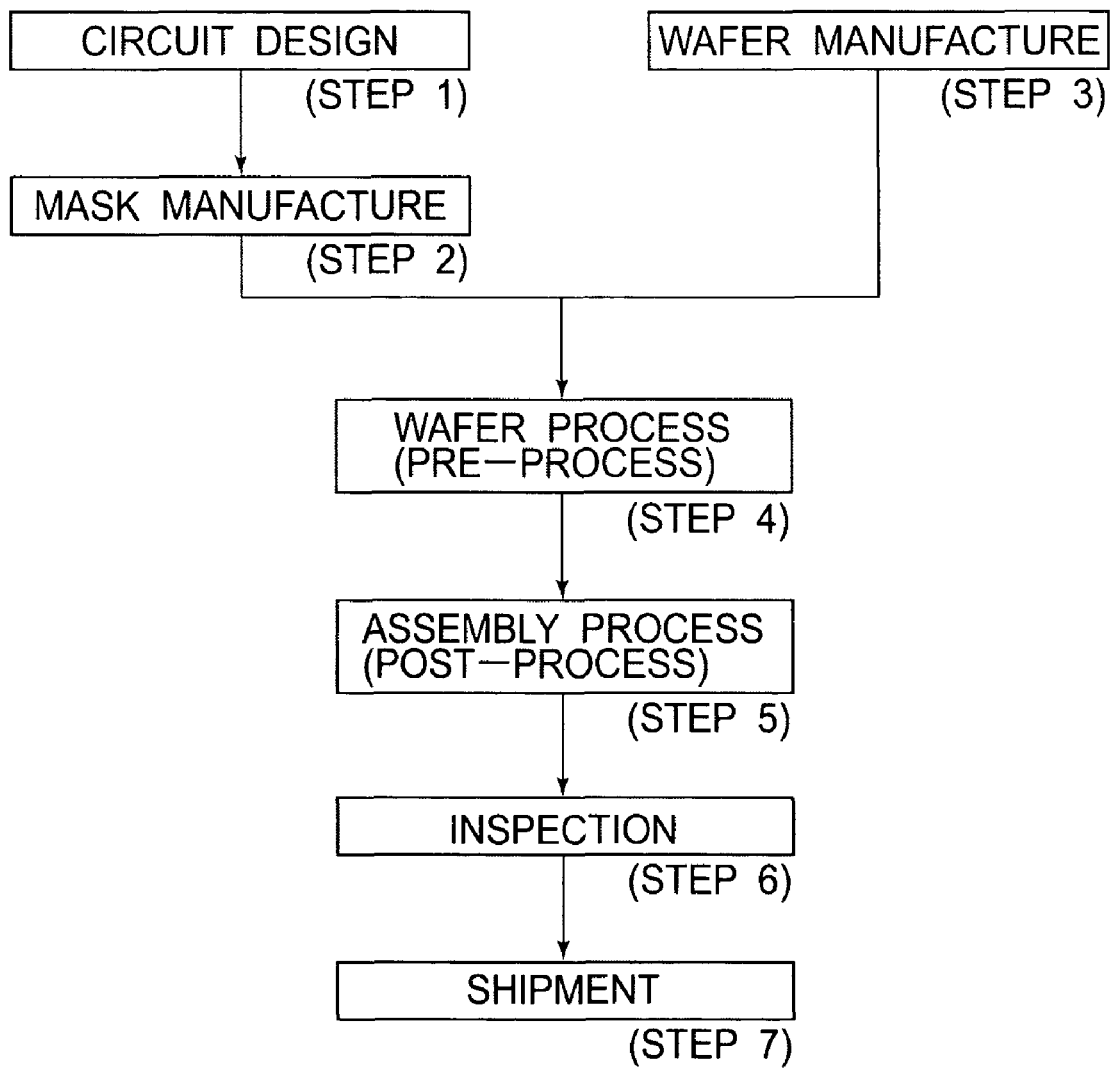
FIG. 7 is a flow chart for explaining the procedure of device manufacturing processes.

FIG. 7 is a flow chart for explaining the overall procedure for semiconductor manufacture. Step 1 is a design process for designing a circuit of a semiconductor device. Step 2 is a process for making a mask on the basis of the circuit pattern design.

On the other hand, Step 3 is a process for preparing a wafer by using a material such as silicon. Step 4 is a wafer process which is called a pre-process wherein, by using the thus prepared mask and wafer, a circuit is formed on the wafer in practice, in accordance with lithography. Step 5 subsequent to this is an assembling step which is called a post-process wherein the wafer having been processed at step 4 is formed into semiconductor chips. This step includes an assembling (dicing and bonding) process and a packaging (chip sealing) process. Step 6 is an inspection step wherein an operation check, a durability check an so on, for the semiconductor devices produced by step 5, are carried out. With these processes, semiconductor devices are produced, and finally they are shipped (step 7).

More specifically, the wafer process at step 4 described above includes: (i) an oxidation process for oxidizing the surface of a wafer; (ii) a CVD process for forming an insulating film on the wafer surface; (iii) an electrode forming process for forming electrodes upon the wafer by vapor deposition; (iv) an ion implanting process for implanting ions to the wafer; (v) a resist process for applying a resist (photosensitive material) to the wafer; (vi) an exposure process for printing, by exposure, the circuit pattern of the mask on the wafer through the exposure apparatus described above; (vii) a developing process for developing the exposed wafer; (viii) an etching process for removing portions other than the developed resist image; and (ix) a resist separation process for separating the resist material remaining on the wafer after being subjected to the etching process. By repeating these processes, circuit patterns are superposedly formed on the wafer.

In accordance with the embodiments of the present invention as described hereinbefore, very useful data which is hidden in massive exposure hysteresis data or inspection data and which cannot be revealed by conventional data mining can be found out quite efficiently. As a result of this, the exposure precision and/or the throughput can be improved significantly.

The present invention can be embodied in various forms, and examples are as follows.

[1] A semiconductor exposure method apparatus wherein a circuit pattern formed on a reticle is brought into alignment with a pattern already formed on a wafer and wherein plural exposures are made to the wafer, having features that: exposure hysteresis data comprising a control variable and measurement data, related to exposure in the semiconductor exposure apparatus, and inspection data measured in relation to the wafer after exposure and development of the wafer are taken as an explanatory variable and a response variable, respectively; correlation between the response variable and the explanatory variable is sought while changing the number of data pieces, and the exposure is carried out while making correction on the basis of one of conditions having high correlation and by using the relationship in that correlation.

[2] A semiconductor exposure method and apparatus according to Item [1] above, wherein the measurement data in the hysteresis data includes not only measurement data of measuring tools such as a wafer alignment measurement condition and a focus measurement condition but also variables such as year, month, date, day of the week, time, temperature, pressure, humidity, machine ID and operators when the exposure operation is carried out, as well as data such as reset, maintenance and the like of the exposure apparatus or process machines.

[3] A semiconductor exposure method and apparatus according to Item [1] above, wherein the inspection data includes not only measurement data obtained by measurement through an inspection tool but also processed data obtained by calculation made to the measured data.

[4] A semiconductor exposure method and apparatus according to Item [1], wherein, when the correlation between the response variable and the explanatory variable is to be taken while changing the number of used data pieces, the correlation is sought by sequentially halving all the data pieces in the order of ½, ¼ and ⅛, and wherein, with regard to an explanatory variable with which the magnitude of correlation has changed, the relationship with the exposure hysteresis data is further mined (searched or dug).

[5] A semiconductor device manufacturing exposure method, wherein a circuit pattern formed on a reticle is brought into alignment with a pattern already formed on a wafer and wherein plural exposures are made to the wafer, having features that: exposure hysteresis data comprising a control variable and measurement data, related to exposure in the semiconductor exposure apparatus, and inspection data measured in relation to the wafer after exposure and development of the wafer are taken as an explanatory variable and a response variable, respectively; correlation between the response variable and the explanatory variable is sought while changing the number of data pieces, and the exposure is carried out while making correction on the basis of one of conditions having high correlation and by using the relationship in that correlation.

[6] A semiconductor exposure method apparatus wherein a circuit pattern formed on a reticle is brought into alignment with a pattern already formed on a wafer and wherein plural exposures are made to the wafer, having features that: exposure hysteresis data comprising a control variable and measurement data, related to exposure in the semiconductor exposure apparatus, and inspection data measured in relation to the wafer after exposure and development of the wafer are taken as an explanatory variable and a response variable, respectively; correlation between the response variable and the explanatory variable is sought while changing the number of data pieces; and, among these, a condition having high correlation is determined and the exposure is carried out while restricting a tolerable quantity for controllability of a corresponding variable in the exposure hysteresis data.

While the invention has been described with reference to the structures disclosed herein, it is not confined to the details set forth and this application is intended to cover such modifications or changes as may come within the purposes of the improvements or the scope of the following claims.

This application claims priority from Japanese Patent Application No. 2005-210320 filed Jul. 20, 2005, for which is hereby incorporated by reference.

What is claimed is:

1. An apparatus comprising:
a computer configured to detect magnitude of correlation between (i) an explanatory variable corresponding to operation data related to an operation made by an exposure apparatus for exposing a substrate, and (ii) a response variable corresponding to inspection data related to a result of inspection made to the substrate after the same is exposed, the magnitude of correlation between the explanatory variable and the response variable being detected with respect to each of plural kinds of operation data; and
wherein said computer is further configured to specify, on the basis of detected correlation magnitudes, the correlation between the explanatory variable and the response variable with respect to each of the plural kinds of operation data, and
wherein said computer is further configured to obtain a plurality of sets of data of the explanatory variable and data of the response variable and to calculate a plurality of the magnitudes of correlation while changing at least one of the number or range of the obtained sets of the data used for calculation of the magnitudes of correlation.

2. An apparatus according to claim 1, wherein the operation data relates to at least one of a control made by the exposure apparatus, a measurement made by the exposure apparatus, a date of operation, an environmental condition for the operation, an ID of the exposure apparatus, reset information of the exposure apparatus, maintenance information of the exposure apparatus, and an ID of an operator of the exposure apparatus.

3. An apparatus according to claim 1, wherein the inspection data relates to at least one of data concerning an overlay error of the pattern formed on the substrate, and data concerning a size error of that pattern.

4. An apparatus according to claim 1, wherein said computer determines a category of the operation data on the basis of the obtained magnitude of correlation, wherein, the category concerns information for categorizing processes for manufacturing a device.

5. An apparatus according to claim 1, further comprising determining means configured to determine a control parameter to be used in the exposure apparatus, on the basis of the correlation specified by said computer.

6. An apparatus according to claim 5, wherein the control parameter concerns at least one of data for correcting control target data to be used in the exposure apparatus, data for correcting measurement data obtained in the exposure apparatus, a tolerable range for the control target data, and a tolerable range for the measurement data.

7. An apparatus according to claim 1, wherein said apparatus is one of an exposure apparatus for performing an exposure of a substrate to a pattern, an inspection apparatus for inspecting a substrate to which the exposure has been performed, and a host computer for controlling an operation of the exposure apparatus.

8. An exposure apparatus for performing an exposure of a substrate to a pattern, said apparatus comprising:
a controller configured to control an operation of said exposure apparatus on the basis of information related to a correlation between (i) an explanatory variable corresponding to data related to an operation made by said exposure apparatus and (ii) a response variable corresponding to inspection data related to inspection made to the substrate after the same is exposed; and
an apparatus for specifying the correlation comprising:
a computer configured to detect magnitude of correlation between (i) an explanatory variable corresponding to operation data related to an operation made by an exposure apparatus for exposing a substrate, and (ii) a response variable corresponding to inspection data related to a result of inspection made to the substrate after the same is exposed, the magnitude of correlation between the explanatory variable and the response variable being detected with respect to each of plural kinds of operation data; and
wherein said computer is further configured to specify, on the basis of detected correlation magnitudes, the correlation between the explanatory variable and the response variable with respect to each of the plural kinds of operation data, and
wherein said computer is further configured to obtain a plurality of sets of data of the explanatory variable and data of the response variable and to calculate a plurality of the magnitudes of correlation while changing at least one of the number or range of the obtained sets of the data used for calculation of the magnitudes of correlation.

9. A method of manufacturing a device, said method comprising steps of:
exposing a substrate to a pattern using an exposure apparatus for performing an exposure of a substrate to a pattern, said exposure apparatus comprising:
a controller configured to control an operation of said exposure apparatus on the basis of information related to a correlation between (i) an explanatory variable corresponding to data related to an operation made by said exposure apparatus and (ii) a response variable corresponding to inspection data related to inspection made to the substrate after the same is exposed; and
an apparatus for specifying the correlation comprising:
a computer configured to detect magnitude of correlation between (i) an explanatory variable corresponding to operation data related to an operation made by an exposure apparatus for exposing a substrate, and (ii) a response variable corresponding to inspection data related to a result of inspection made to the substrate after the same is exposed, the magnitude of correlation between the explanatory variable and the response variable being detected with respect to each of plural kinds of operation data; and
wherein said computer is further configured to specify, on the basis of detected correlation magnitudes, the correlation between the explanatory variable and the response variable with respect to each of the plural kinds of operation data, and
wherein said computer is further configured to obtain a plurality of sets of data of the explanatory variable and data of the response variable and to calculate a plurality of the magnitudes of correlation while changing at least one of the number or range of the obtained sets of the data used for calculation of the magnitudes of correlation;
developing the exposed substrate; and
processing the developed substrate to manufacture the device.

10. A method comprising steps of:
detecting magnitude of correlation between (i) an explanatory variable corresponding to operation data related to an operation made by an exposure apparatus for exposing a substrate, and (ii) a response variable corresponding to inspection data related to a result of inspection made to the substrate after the same is exposed, the magnitude of correlation between the explanatory variable and the response variable being detected with respect to each of plural kinds of operation data; and
specifying, on the basis of detected correlation magnitudes, the correlation between the explanatory variable and the response variable with respect to each of the plural kinds of operation data,
wherein said detecting step comprises obtaining a plurality of sets of a data of the explanatory variable and a data of the response variable and calculating a plurality of the magnitudes of correlation while changing at least one of the number or range of the obtained sets of the data used for calculation of the magnitudes of correlation.

11. An apparatus according to claim 1, wherein the operation data is data concerning an alignment measurement signal, wherein the inspection data is an alignment offset amount, and wherein said computer carries out correction of data concerning the alignment measurement signal based on the correlation.

* * * * *